US010751372B2

(12) United States Patent
Har-Noy

(10) Patent No.: US 10,751,372 B2
(45) Date of Patent: Aug. 25, 2020

(54) VACCINE COMPOSITIONS AND METHODS

(71) Applicant: Immunovative Therapies Ltd, Jerusalem (IL)

(72) Inventor: Michael Har-Noy, Jerusalem (IL)

(73) Assignee: MIRROR BIOLOGICS, INC., Mesa, AZ (US)

( * ) Notice: Subject to any disclaimer, the term of this patent is extended or adjusted under 35 U.S.C. 154(b) by 0 days.

(21) Appl. No.: 16/215,116

(22) Filed: Dec. 10, 2018

(65) Prior Publication Data

US 2019/0105350 A1 Apr. 11, 2019

Related U.S. Application Data

(63) Continuation of application No. 12/434,168, filed on May 1, 2009, now abandoned.

(60) Provisional application No. 61/050,294, filed on May 5, 2008, provisional application No. 61/049,990, filed on May 2, 2008.

(51) Int. Cl.
*A61K 39/39* (2006.01)
*A61K 39/395* (2006.01)
*A61P 31/00* (2006.01)
*C12N 5/0783* (2010.01)
*A61P 35/00* (2006.01)
*A61K 39/00* (2006.01)
*A61P 37/04* (2006.01)
*A61K 35/28* (2015.01)
*A61K 35/12* (2015.01)

(52) U.S. Cl.
CPC .......... *A61K 35/28* (2013.01); *A61K 39/0011* (2013.01); *A61K 39/39* (2013.01); *C12N 5/0636* (2013.01); *A61K 2035/124* (2013.01); *C12N 2501/51* (2013.01); *C12N 2501/515* (2013.01); *C12N 2501/52* (2013.01)

(58) Field of Classification Search
None
See application file for complete search history.

(56) References Cited

U.S. PATENT DOCUMENTS

| | | | |
|---|---|---|---|
| 5,747,024 | A | 5/1998 | Grabstein et al. |
| 5,837,251 | A | 11/1998 | Srivastava |
| 6,136,315 | A | 10/2000 | Srivastava |
| 6,139,841 | A | 10/2000 | Srivastava |
| 6,162,436 | A | 12/2000 | Srivastava |
| 6,187,312 | B1 | 2/2001 | Srivastava |
| 6,797,480 | B1 | 9/2004 | Srivastava |
| 6,875,849 | B2 | 4/2005 | Graner et al. |
| 7,402,431 | B2 | 7/2008 | Har-Noy |
| 7,435,592 | B2 | 10/2008 | Har-Noy |
| 2003/0134415 | A1 | 7/2003 | Gruenberg |
| 2004/0228848 | A1 | 11/2004 | Har-Noy |
| 2005/0191291 | A1 | 9/2005 | Har-Noy |

FOREIGN PATENT DOCUMENTS

| | | |
|---|---|---|
| JP | 2010508364 A | 3/2010 |
| WO | 2006120439 A2 | 11/2006 |
| WO | 2007120128 | 10/2007 |

OTHER PUBLICATIONS

T. A. Waldmann, Immunotherapy: past, present and future, Nature Medicine, vol. 9, No. 3, 2003, pp. 269-277.
T. Boon, et al., Tumor antigens recognized by T lymphocytes, Annual Review of Immunology, vol. 12, 1994, pp. 337-365.
D. M. Pardoll, Tumor reactive T cells get a boost, Nature Biotechnology, vol. 20, 2002, pp. 1207-1208.
J. A. Berzofsky, et al., Progress on new vaccine strategies for the immunotherapy and prevention of cancer, The Journal of Clinical Investigation, vol. 113, 2004, pp. 1515-1525.
J. A. Berzofsky, et al., Progress on new vaccine strategies against chronic viral infections, The Journal of Clinical Investigations, vol. 114, 2004, pp. 450-462.
T. R. Mosmann, et al., TH1 and TH2 cells: different patterns of lymphokine secretion lead to different functional properties, Annual Review of Immunology, vol. 7, 1989, pp. 145-173.
T. Nishimura, et al., The critical role of Th1-dominant immunity in tumor immunology, Cancer Chemotherapy Pharmacology, vol. 46 Suppl., 2000, pp. S52-S61.
E. B. Lindblad, Aluminium compounds for use in vaccines, Immunology and Cell Biology, vol. 82, 2004, pp. 497-505.
A. Podda, et al., MF59-adjuvanted vaccines: increased immunogenicity with an optimal safety profile, Expert Review Vaccines, vol. 2, No. 2, 2003, pp. 197-203.
E. B. Lindblad, Aluminium adjuvants—in retrospect and prospect, Vaccine 22, 2004, pp. 3658-3668.
S. A. Rosenberg, et al., Cancer immunotherapy: moving beyond current vaccines, Nature Medicine, vol. 10, 2004, pp. 909-915.
R. Thimme, et al., A target on the move: innate and adaptive immune escape strategies of hepatitis C virus, Antiviral Research, vol. 69, 2006, pp. 129-141.
M. A. Ostrowski, et al., Why can't the immune system control HIV-1? Defining HIV-1-specific CD4+ T cell immunity in order to develop strategies to enhance viral immunity, Immunologic Research, vol. 35, No. 1-2, 2006, pp. 89-102.
R. S. Kornbluth, et al., Immunostimulatory combinations: designing the next generation of vaccine adjuvants, Journal of Leukocyte Biology, vol. 80, 2006, pp. 1084-1102.
B. H. Segal, et al., Heat shock proteins as vaccine adjuvants in infections and cancer, Drug Discovery Today, vol. 11, Nos. 11/12, 2006, pp. 534-540.
M. W. Graner, et al., Tumor-derived chaperone-rich cell lysates are effective therapeutic vaccines against a variety of cancers, Cancer Immunology Immunotherapy, vol. 52, 2003, pp. 226-234.
G. Li, et al., A chaperone protein-enriched tumor cell lysate vaccine generates protective humoral immunity in a mouse breast cancer model, Mol. Cancer Therapy, vol. 7, 2008, pp. 721-729.

(Continued)

Primary Examiner — Robert A Zeman
(74) Attorney, Agent, or Firm — Westman, Champlin & Koehler, P.A.; Z. Peter Sawicki; Visala C. Goswitz

(57) ABSTRACT

The present invention relates to pharmaceutical vaccine compositions comprising at least one vaccine antigen together with living immune cells. These immune cells include at least a portion of activated T-cells and act as an adjuvant. Methods for using these pharmaceutical compositions to prevent or treat diseases, such as cancer, infectious diseases and autoimmune disease are also included.

6 Claims, 2 Drawing Sheets

(56) References Cited

OTHER PUBLICATIONS

Y. Zeng, et al., Chaperone-rich cell lysates, immune activation and tumor vaccination, Cancer Immunology Immunotherapy, vol. 55, 2006, pp. 329-338.

N. Larmonier, et al., Chaperone-rich tumor cell lysate-mediated activation of antigen-presenting cells resists regulatory T cell suppression, Journal of Leukoccyte Biology, vol. 83, 2008, pp. 1049-1059.

K. L. Kislin, et al. Chaperone-rich cell lysate embedded with BCR-ABL peptide demonstrates enhanced anti-tumor activity against a murine BCR-ABL positive leukemia, FASEB Journal, vol. 21, 2007, pp. 2173-2184.

Concepcion, M. et al., Dendritic cells cross-present HIV antigens from live as well as apoptotic infected CD4+ T lymphocytes, Proceedings of the National Academy of Sciences, Apr. 20, 2004, vol. 101, No. 16, pp. 6092-6097.

Larsson M. et al., Activation of HIV-1 specific CD4 and CD8 T cels by dendritic cells: roles for cross-presentation and non-infectious HIV-1 virus, AIDS, Jul. 5, 2002, vol. 16, No. 10, pp. 1319-1329.

Zhao X.Q et al., Induction of anti-human immunodeficiency virus type 1 (HIV-1) CD8(+) and CD4(+) T-cell reactivity by dendritic cells loaded with HIV-1 X4-infected apoptotic cells, J. Virol., Mar. 2002, vol. 76, No. 6, pp. 3007-3014.

PCT International Search Report, dated Jan. 6, 2010.

Written Opinion, dated Dec. 28, 2009.

Office Action, Israeli Patent Application No. 209027 "Vaccine Compositions and Uses Thereof", dated Nov. 2, 2011.

Office Action, Chinese Patent Application No. 200980125498.1 "Vaccine Compositions and Methods" dated Oct. 8, 2012.

Israeli Office Action for 209027, dated Sep. 12, 2013.

Japanese Office Action for 2011-507708, dated Sep. 3, 2013.

Har-Noy M. & Slavin S.: The anti-tumor effect of allogeneic bone marrow/stem cell transplant without graft vs. host disease toxicity and without a matched donor requirement Med. Hypotheses. 2008; 70(6): 1186-92.

Office Action for related Israeli Patent Application No. 209027, dated Dec. 29, 2015.

Cox J.C. et al., "Adjuvants—a classification and review of their modes of action", Vaccine, Feb. 1997, vol. 15, No. 3, pp. 248-256.

Hiroaki Ikeda et al., "The critical role of type-1 innate and acquired immunity in tumor immunotherapy", Cancer Science, Sep. 2004, vol. 95, No. 9, pp. 697-703.

Har-Noy M et al., "Allogeneic CD3/CD28 cross-linked memory cells provide potent adjuvant effects for active immunotherapy of leukemia/lymphoma", Leukemia Research, Apr. 2009, vol. 33, No. 4, pp. 525-538.

N. Janikashvili et al., "Allogeneic effector/memory Th-1 cells impair Foxp3+ regulatory T lymphocytes and synergize with chaperone-rich cell lysate vaccine to treat leukemia" Blood, Feb. 2011, vol. 117, No. 5, pp. 1555-1564.

T. Nishimura et al., "Distinct Role of Antigen-Specific T Helper Type 1 (Th1) and Th2 Cells in Tumor Eradication in Vivo", Journal of Experimental Medicine, Sep. 1999, vol. 190, No. 5, pp. 617-628.

Yi Zeng et al., "Chaperone-rich cell lysates, immune activation and tumor vaccination", Cancer Immunology Immunotherapy, Mar. 2006, vol. 55, No. 3, pp. 329-338.

Woodland D.L., "Jump-starting the immune system: prime bosting comes of age", Trends in Immunology, Feb. 2004, vol. 25, No. 2, pp. 98-104.

Decision to Refuse a European Patent Application for corresponding EP application No. 09740001.4, dated Mar. 16, 2016.

Shinomiya Y. et al.→ "Anti-Metastatic Activity Induced by the In Vivo Activation of Purified Protein Derivative (PPD)—Recognizing Th1 Type CD4+ Cells" *Immunobiol.* (1995), vol. 193, pp. 439-455.

VACCINE COMPOSITIONS AND METHODS

CROSS-REFERENCE TO RELATED APPLICATION

The present application is a continuation of and claims the benefit of U.S. patent application Ser. No. 12/434,168, filed May 1, 2009, which is based on and claims the benefit of U.S. provisional patent application Ser. No. 61/050,294, filed May 5, 2008 and Ser. No. 61/049,990, filed May 2, 2008, the contents of which are hereby incorporated by reference in their entireties.

FIELD OF INVENTION

The present invention relates to the field of vaccines, and more particularly to adjuvanted vaccine compositions.

BACKGROUND OF THE INVENTION

Harnessing the power of the immune system to treat chronic infectious diseases or cancer is a major goal of immunotherapy. Vaccinations (aka, active immunotherapy) are designed to activate the immune system to specifically recognize and protect against invading pathogens. For over 200 years, active immunotherapy approaches have been used to prevent numerous infectious diseases, including small pox, rabies, typhoid, cholera, plague, measles, varicella, mumps, poliomyelitis, hepatitis B and the tetanus and diphtheria toxins.

Active immunotherapy concepts are now being applied to develop therapeutic cancer vaccines with the intention of treating existing tumors or preventing tumor recurrence, as well as being applied to the treatment and prevention of chronic viral infections. However, existing active immunotherapy technology has not been successful in protecting against many of the modern vaccine targets such as HIV/AIDS, Hepatitis B and cancer. This is in part due to the inability of current vaccination technology to elicit the correct type of immune responses.

The type of immune response generated to infection or other antigenic challenges can generally be distinguished by the subset of T helper (Th) cells involved in the response. Immune responses can be broadly divided into two types: Th1 and Th2. Th1 immune activation is optimized for intracellular infections such as viruses and involves the activation of Natural Killer (NK) cells and Cytolytic T-cells (CTL) that can lyse infected cells, whereas Th2 immune responses are optimized for humoral (antibody) responses. Th1 immune activation is the most highly desired for cancer therapy and Th2 immune responses are directed more at the secretion of specific antibodies and are relatively less important for tumor therapy. Prior art vaccine compositions are specialized in eliciting Th2 or humoral immune responses, which are not effective against cancers and most viral diseases.

The use of adjuvants is a strategy for influencing the immune response to antigens in a vaccine composition. Aluminum salts, and squalene oil in water emulsion (MF59) are the most widely used adjuvants in human vaccines. These adjuvants predominantly promote Th2 humoral (antibody) responses to antigens and are effective at elevating serum antibody titers, but do not elicit significant Th1 responses or CTLs. However, vaccines against chronic infections (e.g., human immunodeficiency virus (HIV), hepatitis C virus (HCV), tuberculosis, herpes simplex virus (HSV)) and cancer cells require generation of Th1 cellular immune responses for protection and therapeutic effect.

Some experimental active immunotherapy techniques and protocols in the prior art have proven to successfully elicit Th1 responses against tumor antigens in select patients, resulting in increased frequencies of CTL immune cells in circulation that have the ability to specifically kill tumors or pathogen infected cells. However, despite the ability to elicit Th1 responses tumor escape mechanisms can overpower this immune response resulting in eventual tumor progression. Viruses have also developed a number of countermeasures to avoid immune attack and stay moving targets for the immune system.

SUMMARY OF THE INVENTION

Figure 1A:
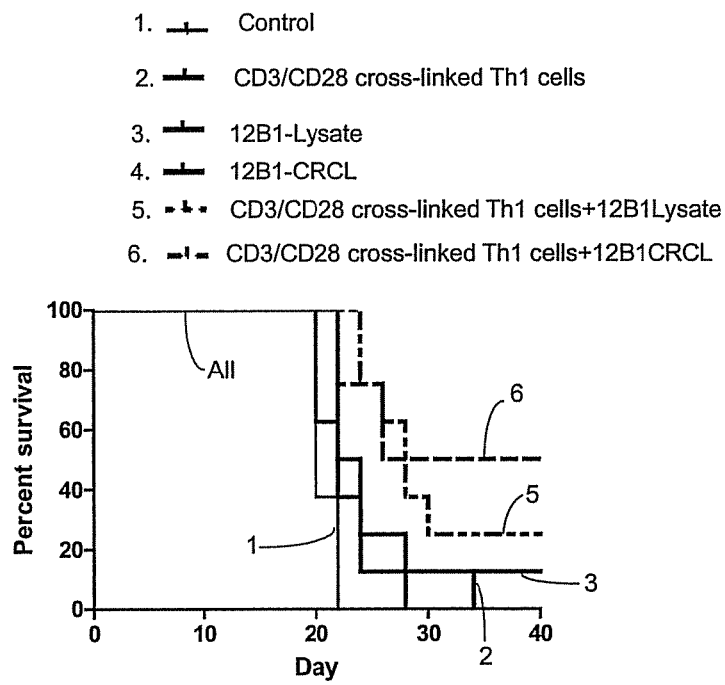
FIG. 1a is a graph of the survival of the mice after administration of the stated compositions.

In one aspect, the present invention includes a pharmaceutical composition. The composition comprises an adjuvant and one or more antigens, wherein the adjuvant comprises living immune cells where at least a portion are activated T-cells. Administration of the composition to a host generates a Th-1 response.

In another aspect, the present invention includes an adjuvant composition comprising living immune cells wherein at least a portion of the immune cells are activated T-cells. The administration of the adjuvant composition to a host elicits a Th-1 immune response.

In yet another aspect, the present invention includes a method of making a pharmaceutical composition. The method includes preparing an adjuvant comprising living immune cells wherein the immune cells comprise at least a portion of T-cells and combining one or more antigens with the adjuvant, wherein the pharmaceutical composition, upon administration to a host, stimulates an immune response in the host.

In a further aspect, the present invention includes a method of reducing antigens related to or causing a disease in a host. The method includes administering a pharmaceutical composition comprising an adjuvant and one or more antigens. The adjuvant includes living immune cells wherein the immune cells comprise at least a portion of T-cells, and wherein the pharmaceutical composition, upon administration to the host, stimulates an immune response in the host.

In yet another aspect, the present invention includes a method of treating a disease in a patient. The method includes administering a pharmaceutical composition comprising an adjuvant and one or more antigens. The adjuvant includes living immune cells wherein the immune cells comprise at least a portion of T-cells, and wherein the pharmaceutical composition, upon administration to the patient, stimulates an immune response in the host.

DETAILED DESCRIPTION OF THE PREFERRED EMBODIMENTS

The present invention provides pharmaceutical vaccine compositions and methods for active immunotherapy that are capable of eliciting protective and therapeutic Th1 immunity in patients against diseases while also providing the means to overcome the immunoavoidance mechanisms of the disease pathogens and tumors. The pharmaceutical composition of the present invention generally includes: (1) one or more sources of antigen; and (2) living, activated immune cells whereby at least a portion are T-cells.

In the present invention, a new vaccine adjuvant for patients is described. The adjuvant can be mixed together with one or more vaccine antigens to form a pharmaceutical composition. In some embodiments, the adjuvant can be used alone as an immunostimulant. The novel adjuvant comprises living immune cells, where at least a portion are T-cells. The T-cells are preferably memory T-cells (CD45RO+, CD62L$^{Lo}$) of the Th1 phenotype (CD4+ T-cells that produce IFN-γ and not IL-4). The memory Th1 cells are activated at the time of formulation and introduction to a patient. The preferred activation method is by the cross-linking of CD3 and CD28 surface molecules on the T-cells. Other activation methods are also within the scope of the invention. The activated memory T-cells preferably express CD40L upon being activated and produce large amounts of inflammatory cytokines (such as IFN-γ, GM-CSF, and TNF-α). These activated Th1 memory cells are preferably allogeneic to the patient.

A pharmaceutical vaccine composition generally contains at least one antigen mixed together with an adjuvant. According to the prior art, it is known practice to increase the immune response induced by the antigens present in a vaccine by means of adjuvants. Adjuvants, as referred to herein, are compounds that can increase the intrinsic immunogenicity of an antigen. The term "adjuvant" is also often used as a synonym for "immunostimulant".

Adjuvants for new vaccine targets such as cancer and infectious diseases are required not only to increase the immunogenicity to vaccine antigens, but are also often required for the deviation of an existing immune response against the vaccine antigen from Th2 to Th1. Additionally, efficacy of the vaccine often requires amplification of this deviated immune response. The vaccine adjuvant composition of this invention provides these immunomodulatory and immunopotentiation properties.

Several adjuvants are known for promoting Th1 immunity to an antigen including: saponins, BCG, liposomes and microparticles, poly I:C, anti-CD40 mAbs, co-stimulatory molecules, IC31, TLR9 ligands, KLH, CpG, α-galactosyl-ceramide, TLR4 agonists, cholera toxin, cytokines, chemokines, immune-stimulating complexes (ISCOMs), LPS, molecular agonists (e.g., agonists for NAIP, CITTA, HET-E, TP-1-leucine-rich repeat pathway receptors), TNF receptor superfamily (TNFRSF) agonists, alarmins and blockers of immunosuppressive cytokines and Tregs. These adjuvants each have the ability to operate at one level of the cascade of immunological events necessary for immunomodulation or immunostimulation or for disabling of immune avoidance. However, none of these adjuvants have the necessary properties to have all these effects.

The present invention relates to the discovery that activated immune cells, preferably, allogeneic Th1 memory cells activated by cross-linking CD3 and CD28 antigens that produce inflammatory cytokines and express CD40L, can elicit all the components in the immune cascade necessary to act as a potent immunomodulator and immunostimulator. In addition, these activated immune cells can be capable of interfering with suppressive regulatory mechanisms in order to overcome the ability of pathological organisms and cancers to evade immune attack. This makes these cells an ideal adjuvant.

The pharmaceutical composition of one or more vaccine antigens with activated T-cells cells may be used for prophylactic purposes or therapeutic purposes, or else both. The composition may be administered via all the routes conventionally used or recommended for vaccines: including the parenteral, intradermal, intramuscular, subcutaneous or mucosal routes. In certain embodiments, the composition may also be administered intranodally or intratumorally.

The antigen component of the pharmaceutical composition includes one or more antigens. If more than one antigen is included in the pharmaceutical composition, the antigens may be from the same antigen source or different antigen sources. Any antigen source can be used in the formulation, for example these antigens can be sourced from living cells or organisms, the source material can be freeze/thaw lysates, irradiation inactivated (or other inactivation method), used as whole cells or organisms or lysates therefrom. In some preferred embodiments, tumor cells or tumor cell lysates can serve as the cell source material for the antigens. The cell source material can be derived from autologous or allogeneic cell sources or from cell lines. Antigens can also be sourced from naked DNA or RNA, which encode for antigens. The nuclear material can be used alone or incorporated with viral vectors. Another example of antigen source is anti-idiotypic antibodies or portions thereof that mimic antigens, or other methods to mimic the structure of an antigen. Antigen-pulsed or transfected dendritic cells (DC) can also be an antigen source in the pharmaceutical composition. The DC can be pulsed with peptides or whole proteins, recombinant proteins, or mRNA or DNA encoding for antigen(s), or the DC can be fused with cells containing the antigens, or the DC can be transfected with viral vectors such as retrovirus, lentivirus, adenovirus which contain the antigen, or these antigen source components can be used alone without the DC.

One or more tumor associated antigens (TAA) can also be used in the pharmaceutical composition, examples of TAA include: MART-1, gp100, tyrosinase, Melan A, TRP-1, tumor-specific mutated gene products, such as CDK-4, β-catenin, MUM-1, oncogenes such as p53, and ras (K- and H-ras), cancer testes antigens, such as MAGE, GAGE and NY-ESO1, over-expressed self antigens such as MUC1, cyclin B1, Her2-neu, CEA, WT, p53, SART-1, PRAME, p15, and viral antigens such as HPV E7, EBV-derived antigens and telomerase.

In a preferred embodiment, the antigenic component can include one or more chaperone proteins (also known as heat shock proteins) isolated from dead infected tissue or tumors. Heat shock proteins (HSP) are among the major targets of the immune response to bacterial, fungal and parasitic pathogens. Tumor derived heat shock protein (hsp)-peptide complexes (particularly hsp70 and grp94/gp96) have been demonstrated to serve as effective vaccines, producing anti-tumor immune responses in animals and in man. This approach utilizes the peptide binding properties of stress proteins which are responsible for their functions as molecular chaperones in numerous cellular processes.

Certain chaperones in extracellular milieu can also be capable of modulating innate and adaptive immunity due to their ability to chaperone polypeptides and to interact with the host's immune system, particularly professional antigen-presenting cells. Vaccination with HSP from tumors can elicit an anti-tumor response, and down-regulate immune suppression mechanisms. The immunogenicity of HSPs can be derived from the antigenic peptides with which they associate.

A preferred method for isolation of chaperone proteins for use as an antigen source is described by Katsantis in U.S. Pat. No. 6,875,849. Additional methods are described by Srivastava in U.S. Pat. Nos. 6,797,480; 6,187,312; 6,162,436; 6,139,841; 6,136,315; and 5,837,251. The HSP can also be pulsed with antigens, including peptides, whole cells or cell lysates.

In one embodiment, tumor-derived Chaperone Rich Cell Lysate (CRCL) is used as an antigen source and is obtained by the enrichment of the major chaperone proteins from tumor lysate using a free solution-isolectric focusing (FS-IEF) technique as described in the Examples below. This technique is a rapid and efficient procedure for obtaining up to 5 to 20 times more antigenic material and in less time compared to conventional techniques. The FS-IEF method of multiple chaperone complex enrichment can be desirable from a clinical standpoint in terms of high yield from a potentially limited tumor source, and with a rapid turn-around time from tumor harvest to treatment of the patient.

There are a number of advantages in using CRCL-associated peptides as a source of tumor antigen. First, they do not require the identification of tumor specific peptides. Second, they elicit polyclonal T lymphocyte responses following immunization, preventing the outgrowth of immunological escape variants. Third, they consist of both MHC Class I associated peptides and MHC Class II or helper epitopes which together induce more potent and durable immune responses. In numerous animal models, including the murine 12B1 leukemia and the A20 B cell leukemia/lymphoma, CRCL vaccines have demonstrated a clear anti-tumor effect.

In addition, the antigens conventionally used in vaccines can also be used in the pharmaceutical composition of the present invention, including whole microorganisms or part(s) of the microorganisms such as live attenuated whole microorganisms, inactivated microorganisms, recombinant peptides and proteins, glycoproteins, glycolipids, lipopeptides, synthetic peptides, or ruptured microorganisms, polysaccharides, used alone or conjugated to carrier elements, such as carrier proteins, can also be used.

In general, any antigen or combination of antigens that are capable of being used for the treatment or prevention of diseases can be used in the pharmaceutical composition. Antigens derived from infectious pathogens can also serve as antigen sources and may be referred to herein as disease causing antigens. Examples of diseases from which antigens can be sourced are: diphtheria, tetanus, polio, rabies, whooping cough, hepatitis A, B and C, EBV, CMV, herpes 1 and 2, yellow fever, typhoid fever, chicken pox, variola (small pox), measles, mumps, German measles, Japanese encephalitis, meningitis, influenza, pneumococcal infections, rotavirus infections, AIDS (HIV1 and 2), cancers, HTLV1 and 2, syphilis, HPV, tuberculosis, Lyme disease, RSV infections, Trypanosomiasis, Dengue fever, malaria, anthrax, ebola virus, tularemia, *Yersinia*, West Nile virus, bacterial ailments caused by *Chlamydia, Neisseria* gonorrheae, *Streptococcus pneumoniae, Moraxella catarrhalis, Staphylococcus aureus* or *Haemophilus* influenza type B, malaria, leishmaniasis, listeriosis, etc.

The activated Th1 memory cells used in the pharmaceutical compositions of the present invention are preferably derived from normal donor blood. Preferred methods for processing and production of cells suitable for use in the present invention are described by Har-Noy in U.S. Pat. Nos. 7,435,592 and 7,402,431 and pending US patent no. 20050191291 which are incorporated herein by reference in their entirety.

The pharmaceutical composition according to the present invention may be a composition intended for immunization against a single pathogen or cancer, i.e. it comprises one or more antigens from a single pathogen or cancer. Alternatively, it may be a composition intended for immunization against several different pathogens or cancers, referred to herein as a vaccine combination.

The present invention also includes methods of making pharmaceutical compositions. The method includes preparing an adjuvant that includes T-cells, preferably activated T-cells described herein. One or more antigens can be combined with the adjuvant to form the pharmaceutical composition. If more than one antigen is included in the composition, the antigens may be from the same antigenic source or different antigenic sources. Administration of the pharmaceutical composition can stimulate an immune response, preferably a Th-1 response in the host.

The adjuvant action of the activated T-cells can be obtained either when they are combined with the antigen(s) of the pharmaceutical composition prior to being administered, i.e. when it is present directly in the pharmaceutical composition. Alternatively, adjuvant and the antigen(s) can be administered separately, in sequential steps. For example, the adjuvant may first be administered to the host using any one of the techniques described above. After administration of the adjuvant, the host may be administered the antigen(s). Preferably, the adjuvant and the antigen(s) are combined to form one pharmaceutical composition prior to being administered to the host.

The pharmaceutical compositions of the present invention are designed to generate adaptive Th1 immunity to the antigens in the composition. When administering the pharmaceutical composition of the present invention to patients with existing disease, it may be desirable to stimulate a potent innate immune response in order to control disease until the adaptive immune response becomes potent enough to have a therapeutic effect. To accomplish this, the adjuvant immune cells alone can be administered intravenously at the same time or anytime after the vaccine composition is administered.

If the immune response to the vaccine antigens in the composition is not potent enough, additional booster injections may be administered. Preferably the booster injections can be made at least 3-7 days apart, and more preferably 7-14 days apart. Additional booster injections may be administered as needed on a monthly or yearly basis.

In order to maintain an inflammatory environment that is capable of disabling the ability of tumors and disease organisms to evade immune destruction, additional booster injections of activated Th1 memory cells alone or formulated with antigen can be administered. Patients that have been previously vaccinated with a composition containing allogeneic Th1 memory cells can develop anti-alloantigen immunity. Subsequent injections of allogeneic cells can activate the pool of anti-alloantigen cells that can release the inflammatory cytokines necessary for disabling immune avoidance mechanisms.

EXAMPLES

Example 1

Mice

Female BALB/c (H2$^d$) mice were obtained from the National Cancer Institute (Bethesda, Md.) and used at the age of 7 weeks.

Preparation of Th-1 Cells (CD3/CD28 Cross-Linked Th1 Cells)

Spleen cells from Balb/c mice were harvested and treated with ammonium chloride-potassium (ACK) buffer for lysis of red blood cells. Approximately 70-100 million cells were isolated per spleen. CD4+ T-cells were then purified by positive selection (purity>98%) using CD4 immunomagnetic particles on an MS column (Miltenyi Biotec, Germany), approximately 8-12 million CD4 cells were isolated with a yield of 50-60%. Th1 memory cells were generated by expansion with anti-CD3 and anti-CD28-coated paramagnetic beads (CD3/CD28 T-cell expander beads, Dynal/Invitrogen) at an initial bead:CD4 cell ratio of 3:1. The purified CD4 cells were incubated with 20 IU/mL recombinant mouse (rm)IL-2, 20 ng/mL rmIL-7, and 10 ng/mL rmIL-12 (Peprotech, N.J.) and 10 µg/mL antimurine IL-4 mAb (Becton Dickenson) in RPMI 1640 media containing 10% FBS, penicillin-streptomycin-glutamine, nonessential amino acids (NEAA) (Biological Industries, Israel) and 3.3 mM N-acetyl-cysteine (NAC; Sigma) (complete media). Additional cytokine-containing complete media with rmIL-2 and rmIL-7 was added to the CD4 cultures daily from days 3 to 6 to maintain the cell concentration between 0.5 and 1×10$^6$ cells/mL. Additional CD3/CD28 beads were added daily from day 3 to day 6. The number of beads added was calculated to maintain a 1:1 bead:cell ratio as the cells expanded. After 6 days in culture, the CD4 cells expanded approximately 80 to 100-fold and were harvested and debeaded by physical disruption and passage over a magnet. The phenotype of the harvested cells used in experiments were >95% CD4+, CD45RB$^{lo}$, CD62L$^{lo}$, CD44$^{hi}$ and are thus referred to as "memory cells".

CD3/CD28 Cross-Linking

After harvest and prior to injection, de-beaded Th1 memory cells were cultured at a density of 2×10$^6$ cells/ml in cRPMI for 4-6 hours at 37° C. in 5% CO$_2$ with CD3/CD28 mAb conjugated microparticles (T-cell expander, Dynal/Invitrogen) at a 2:1 bead:cell ratio. After 4 h, the cells produced IFN-γ and upregulated the expression of CD40L and FasL on the cell surface. Cross-linked Th1 memory cells used in these experiments expressed FasL and CD40L on the cell surface and produced in excess of 2000 ng/ml/10$^6$ cells/6 h IFN-γ and less than 20 pg/ml IL-4 per 10$^6$ cells/6 h.

12B1 Cell Line

The murine leukemia cell line 12B1 was obtained by retroviral transformation of BALB/c bone marrow cells with the human bcr-abl (b$_3$a$_2$) fusion gene. These cells express the p210 bcr-abl protein. The cells were cultured at 37° C. and in 5% CO$_2$ in RPMI medium (Gibco/BRL, Gaithersburg, Md.) supplemented with 10% heat-inactivated fetal bovine serum (Gemini Bio-products, Woodland, Calif.). Cells were tested routinely and found to be free of *Mycoplasma* contamination

Generation of 12B1 Tumors

For injection, 12B1 cells were first washed 3 times in PBS (Gibco/BRL), then counted and adjusted to a concentration of 5×10$^4$ cells/mL. Female BALB/c mice were injected with 0.1 mL (5×10$^3$ cells) subcutaneously in the right groin and were monitored for tumor development

Preparation of 12B1 Tumor Lysate

Tumor cell pellet from 12B1 cell culture was subjected to 6 freeze/thaw cycle in liquid nitrogen/37° C. water bath. Cell Lysis was verified using Trypan Blue exclusion. Protein concentrations were determined using BCA assays. Proteins were diluted to 25 µg/100 µl in sterile PBS for immunization of mice

Preparation of 12B1 Chaparone-Rich Cell Lysate (CRCL)

Tumors from 12B1 bearing mice were homogenized in 10 mM Tris-Cl (pH 7.4)/10 mM NaCl, 0.1% detergents (equal parts Triton X-100, Triton X-114 and Igepal CA-600, Sigma, St. Louis, Mo.), including 2 µg/ml leupeptin, 0.1 mg/ml Perfabloc, 0.5 mM phenylmethylsulfonate and one complete protease inhibitor cocktail tablet (all from Roche Molecular Biochemicals, Indianapolis, Ind.) in a glass-teflon homogenizer at a ratio of 1 g tumor/5 ml buffer. The homogenate was centrifuged at 10,000 g, 4° C. for 30 min, and samples were taken that are referred to as "lysate." The "lysate" (supernatant) was subsequently centrifuged at 100,000 g, 4° C. for 60 min. The "high speed" supernatant was dialyzed into sequentially lower concentrations of homogenization buffer, ending in water. Protein concentration was determined using colorimetric bicinchoninic acid assays (BCA Reagent, Pierce Endogen, Rockford, Ill.), and the free solution-isoelectric focusing (FS-IEF) starting material was frozen in 25 mg aliquots. FS-IEF was performed with the following modifications: we have replaced ampholytes with Rotolytes (Bio Rad Laboratories, Hercules, Calif.) and used pH ranges of 3.9-5.6, 4.5-6.1 and 5.1-6.8 (5 ml of each A and B reagent for each pH range for a total of 30 ml); we have reduced detergent concentrations to 0.1% each for Triton X-100, Triton X-114 and Igepal CA-600; we loaded only 25 mg of starting material per 60 ml total volume of the isofocusing mixture rather than 50 mg/60 ml. Urea concentration (6 M) was kept the same, and isofocusing conditions were also kept the same (15 W constant power), but the length of IEF was extended to 5 h. SDS-PAGE and Western blot analyses of the fractions were performed and fractions that contained all four of the major immunogenic chaperones (GRP94/gp96, HSP90, HSP70 and calreticulin) were pooled and dialyzed against 2 M urea in 0.1×PBS, pH 7.4, followed by dialysis into 0.1×PBS. Protein concentrations were determined using BCA assays with bovine serum albumin as standard, and proteins were diluted to 25 µg/100 µl in sterile PBS for immunization of mice.

Preparation of Liver CRCL

Liver CRCL was prepared form the liver of the naïve Balb/c mice using the procedures described above. Proteins were diluted to 25 µg/100 µl in sterile PBS for immunization of mice.

Preparation of TuLy CRCL (12B1 Tumor Lysate/Liver CRCL)

12B1 tumor lysate and Liver CRCL were mixed at a 1:1 µg ratio and the mixture was incubated at 4° C. overnight. Proteins were diluted to 50 µg/100 µl in sterile PBS for immunization of mice.

Prophylactic Vaccination of the Mice

80 Balb/c mice (8 mice per group, 10 groups) were used. Mice were vaccinated intra-dermally (i.d.) in the footpad on day −14 and −7 before tumor cell inoculation. The groups were as follows:

Control: PBS 100 µl i.d.
12B1 lysate: 25 µg/100 µl per mouse i.d.
Liver CRCL: 25 µg/100 µl per mouse i.d.
12B1 CRCL: 25 µg/100 µl per mouse i.d.

TuLy CRCL (12B1 tumor lysate/liver CRCL): 50 µg/100 µl per mouse i.d.

Activated Th-1 cells: $1\times10^5$ cells in 100 µl of PBS per mouse i.d.

Activated Th-1 cells+12B1 lysate: $1\times10^5$ cells+25 µg lysate in 100 µl of PBS per mouse i.d.

Activated Th-1 cells+Liver CRCL: $1\times10^5$ cells+25 µg liver CRCL in 100 µl of PBS per mouse i.d.

Activated Th-1 cells+12B1 CRCL: $1\times10^5$ cells+25 µg 12B1 CRCL in 100 µl of PBS per mouse i.d.

Activated Th-1 cells+TuLy CRCL–$1\times10^5$ cells+50 µg TuLy CRCL in 100 µl of PBS per mouse i.d.

Inoculation of Tumor Cells and Monitoring of Tumor Volume

Mice from all 10 groups were inoculated s.c. on the right groin on day 0 with 5000 12B1 cells/mouse. Tumor volume was determined every 2 days. Mice were euthanized when tumor volume reaches 4000 mm$^3$.

Results

Figure 1B:
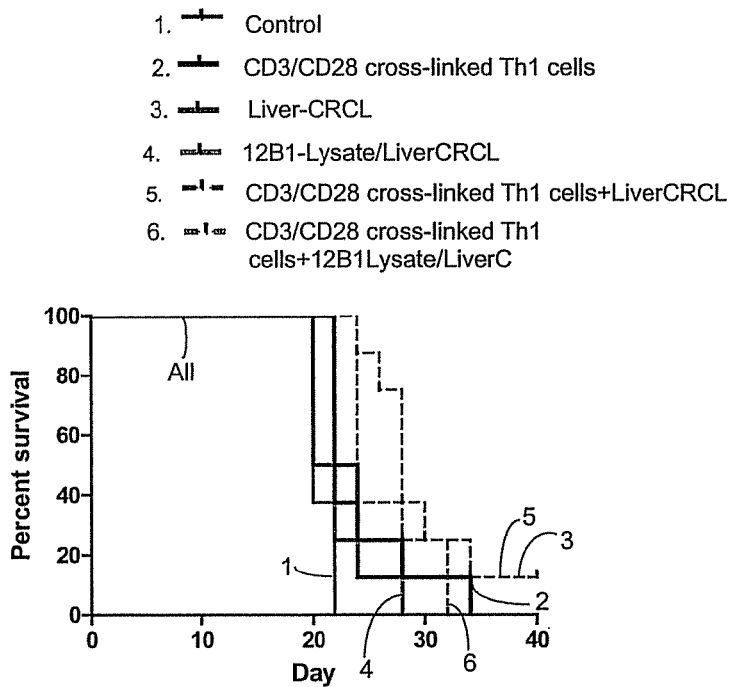
FIG. 1b is a graph of the survival of the mice after administration of the stated compositions.

Tumors became palpable at day 12 in the control group. Results from the various therapies are shown in FIG. 1a and FIG. 1b.

After 6 weeks all mice were dead in the control, CD3/CD28 cross-linked Th1 cells, 12B1 CRCL, Liver CRCL, 12B1-Lysate/liver CRCL and CD3/CD28 cross-linked Th1 cells+12B1-Lysate/liver CRCL groups. 50% of the mice were tumor-free in the combination CD3/CD28 cross-linked Th1 cells+12B1 CRCL group (best group), 25% in the CD3/CD28 cross-linked Th1 cells+12B1 lysate group, 12.5% in the 12B1 lysate group and 12.5% in the CD3/CD28 cross-linked Th1 cells+liver CRCL group.

There is thus a clear benefit in associating CD3/CD28 cross-linked Th1 cells and tumor-derived CRCL.

Example 2

In this example, the tumor-derived CRCL are used as a source of tumor-specific antigens and combined with activated CD4+Th-1 cells as an adjuvant to treat established leukemia. The methods are as described above in Example 1.

Animals (8 mice per group) received the indicated treatments.

Figure 2B:
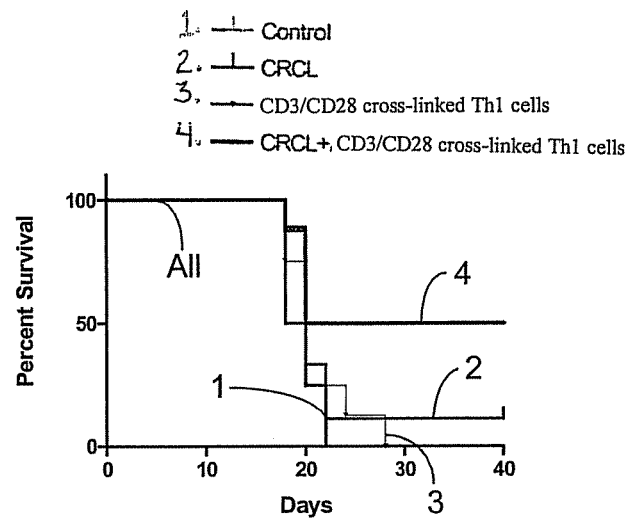
FIG. 2b is a graph of the survival of the mice after administration of the indicated composition.
Figure 2A:
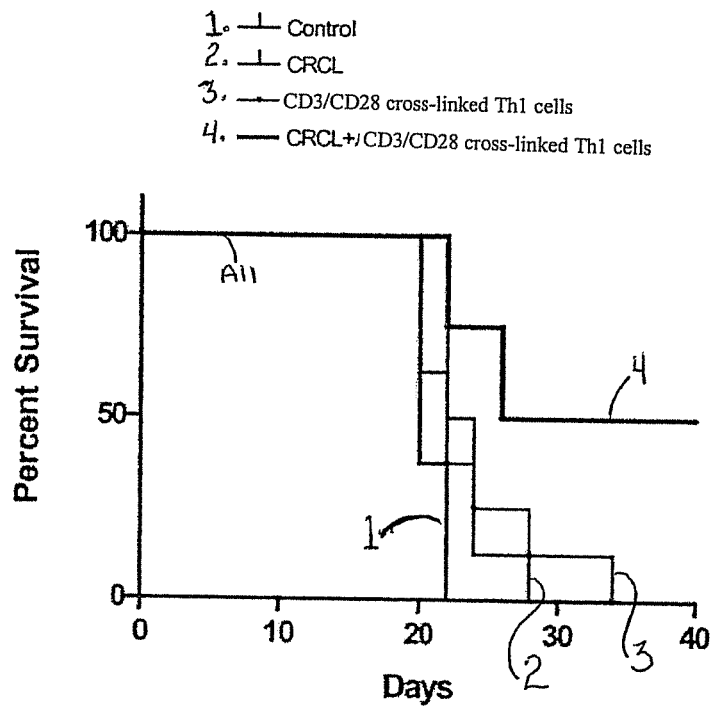
FIG. 2a is a graph of the survival of the mice after administration of the indicated composition.

Prophylactic Setting:

Naïve Balb/c mice were treated by footpad (intradermal) injection at days −14 and −7 with PBS (control), or 12B1-derived CRCL (12B1 CRCL, 25 µg/mouse), or CD3/CD28 cross-linked Th1 cells, or by 12B1 CRCL plus CD3/CD28 cross-linked Th1 cells. On day 0 mice were inoculated with 12B1 leukemia cells (5,000 cells/mouse, s.c. injection in the left groin). Percent survival is shown in FIG. 2A.

Therapeutic Setting:

To define the therapeutic efficacy of CRCL plus CD3/CD28 cross-linked Th1 cells combination, 12B1 tumors (inoculation of 5000 12B1 cells/mouse in the left groin at day 0) were established. Mice were treated on days 3, 7 and 14 with PBS, 12B1 CRCL, CD3/CD28 cross-linked Th1 cells alone or CD3/CD28 cross-linked Th1 cells plus CRCL. Percent survival of mice is depicted in FIG. 2B.

The results indicate that in both settings, the combination of CD3/CD28 cross-linked Th1 cells plus CRCL significantly improves mouse survival compare to CRCL or CD3/CD28 cross-linked Th1 cells monotherapies.

Although the present invention has been described with reference to preferred embodiments, workers skilled in the art will recognize that changes may be made in form and detail without departing from the spirit and scope of the invention.

What is claimed is:

1. A pharmaceutical composition comprising an adjuvant and a chaperone rich cell lysate (CRCL), wherein the adjuvant comprises living immune cells where at least a portion are activated T-cells in infusion media with cross-linked CD3 and CD28 surface molecules;
   wherein the source of the CRCL is a malignant tumor and the CRCL comprises multiple chaperone complexes enriched by free solution-isoelectric focusing; and
   wherein the administration of the composition to a host generates a Th-1 response.

2. The composition of claim 1 wherein the T-cells are memory T-cells of the Th-1 phenotype.

3. The composition of claim 1 wherein the cross-linking of the CD3 and CD28 surface molecules on the T-cells is by anti-CD3 and anti-CD28 monoclonal antibodies.

4. The composition of claim 1 wherein the activated T-cells express CD40L.

5. The composition of claim 1 wherein the T-cells are allogeneic to the host.

6. The composition of claim 1 further comprising one or more tumor associated antigens.

* * * * *